United States Patent
Asp

(10) Patent No.: US 6,436,913 B1
(45) Date of Patent: Aug. 20, 2002

(54) USE OF ESTRAMUSTINE PHOSPHATE IN THE TREATMENT OF BONE METASTASIS

(75) Inventor: Beryl Asp, Bridgewater, NJ (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/625,540

(22) Filed: Jul. 25, 2000

(51) Int. Cl.⁷ ................................................ A61K 31/66
(52) U.S. Cl. ...................... 514/102; 514/103; 514/108; 514/171; 424/450
(58) Field of Search ................................. 514/102, 103, 514/108, 171; 424/450

(56) References Cited

U.S. PATENT DOCUMENTS 4,634,691 A * 1/1987 Hedglin et al. ............. 514/108
5,767,110 A   6/1998 Klohs et al.

\* cited by examiner

*Primary Examiner*—Frederick Krass
(74) *Attorney, Agent, or Firm*—Oblon Spivak, McClelland, Maier & Neustadt, P.C.

(57) ABSTRACT

Estramustine phosphate is shown to act as an inhibitor of bone resorption and can thus be used to treat, prevent or alleviate the symptoms of bone metastasis which arise due to said bone resorption.

39 Claims, No Drawings

USE OF ESTRAMUSTINE PHOSPHATE IN THE TREATMENT OF BONE METASTASIS

The present invention relates to the use of estramustine phosphate in the treatment of bone metastasis, particularly in the treatment of bone metastasis in patients with prostate cancer.

Although the success rate for curing primary cancers is increasing, metastasis remains a limiting factor in antitumour therapy. Metastasis involves the spread of cancer cells from the primary cancer site to a secondary location elsewhere in the body. A common secondary site for metastasising tumour cells is in the bone. The presence of malignant cells in bone induces metabolic bone disease leading, for example, to bone resorption. The clinical symptoms of bone metastasis such as bone pain are partly linked to bone resorption. It has therefore been found that bisphosphonates, which are specific inhibitors of osteoclast-mediated bone resorption, can relieve bone pain in patients with skeletal metastases from prostate cancer. Estramustine phosphate (The Merck Index, XII Ed., No. 3749, 1996) is an estradiol-17β-phosphate derivative widely known in the art as an antitumor agent, currently used in the treatment of advanced adenocarcinoma of the prostate.

As an example, initial intravenous administration of estramustine phosphate, followed by oral administration, has been reported at dosages paralleling the oral administration for the drug, i.e. 300–600 mg daily given intravenously and usually repetitively over for several consecutive days, or as a once weekly high dose of 1000–2500 mg/m$^2$ (see, for a reference, British Journal of Urology, 1977, 49, 73–79; J. Urol. 108:303–306, 1972; Eur. Clin. Pharmacol. 26(1), 113–119, 1984; Eur. Urol. 1990, 17, 216–218).

It has now been found that the intravenous estramustine phosphate can inhibit bone resorption and is thus useful in treating the symptoms of bone metastasis. Accordingly, the present invention provides the use of estramustine phosphate in the manufacture of a medicament for intravenous use as an inhibitor of bone resorption, for instance osteoclast-mediated bone resorption. The invention also provides a method of inhibiting bone resorption in a patient in need of such treatment, which method comprises the intravenous administration to the said patient of an effective amount of estramustine phosphate. The condition of the patient may thereby be improved. The invention also provides an agent for inhibiting bone resorption comprising intravenous estramustine phosphate.

In a particular embodiment of the present invention the medicament containing estramustine phosphate is used to treat, prevent or alleviate the symptoms of bone metastasis. The bone metastasis results from cancer elsewhere in the body, for example prostate cancer, breast cancer, melanoma, lung cancer, pancreatic cancer, colorectal cancer, ovarian cancer and cancers of the brain. In particular, the medicament is for treating, preventing or alleviating the symptoms of bone metastasis in a prostate cancer patient. More in particular, the medicament prevents or alleviates symptoms of pain associated with bone metastases and risk of pathological fractures. In the present invention, estramustine phosphate may be administered in the form of a pharmaceutically acceptable salt, for instance as sodium salt or as a salt with a basic amino acid, e.g. arginine, or with N-methyl glucamine, otherwise referred to as meglumine.

The dosage regimen for the compounds and/or compositions containing the compounds is based on a variety of factors, including the type, age, weight, sex and medical condition of the patient; the severity of the condition; the route of administration; and the activity of the particular compound employed. Thus the dosage regime may vary widely.

According to an embodiment of the invention, the estramustine phosphate formulation can be administered to patients either as a slow injection, e.g. over about 30 minutes to about 3 hours, or as a bolus injection, also referred to as IV (intravenous) push. The intravenous formulations of the present invention are prepared according to conventional techniques adopted in the preparation of pharmaceutical forms for parenteral use. Typically, a proper amount of estramustine phosphate, either as a dry powder or in a lyophilised form, is dissolved in a pharmaceutically acceptable solution for parenteral use.

As an example, a proper amount of estramustine phosphate in the form of a suitable salt such as, for instance, N-methyl glucamine salt, is dissolved in a suitable amount of sterile water or aqueous dextrose solution, e.g. 5% dextrose in water for intravenous administration.

Likewise, a proper amount of estramustine phosphate is dispersed in water and then dissolved by adding at least an equimolar amount of a basic amino acid, for instance arginine. A further amount of the given amino acid, e.g. arginine, can be present in order to reach an estramustine phosphate:arginine molar ratio higher than 1:1, respectively.

Alternatively, a proper amount of estramustine phosphate in the form of a pharmaceutically acceptable salt for parenteral use, e.g. estramustine phosphate meglumine salt, either as a dry powder or into a lyophilised form, is dissolved in a pharmaceutically acceptable solution for parenteral use, for instance sterile water or aqueous dextrose solution, e.g. 5% dextrose in water for intravenous administration, and then admixed with a proper amount of a basic amino acid, for instance arginine. The above mixture is then stirred, sterilised, and subsequently lyophilised according to conventional techniques. The freeze-dried formulation is prepared and stored in vials for injection; the addition of a proper amount of sterile water or a physiological solution for parenteral use enables the preparation of the final formulation to be injected.

The above method is also suitable for preparing high dosage estramustine phosphate formulations. The unit-strength of the formulation to be injected depends on the concentration of the active in the solution itself and, of course, on the filling volume of the vials used to prepare the final formulation.

The formulations comprising estramustine phosphate may optionally contain additional pharmaceutically acceptable excipients for parenteral administration such as, for instance, bulking agents, e.g. lactose or mannitol, pH buffering agents, anti-oxidant agents, preservative agents, tonicity adjusters and the like.

The formulations of the present invention allow the administration of the active principle either as a single agent or, alternatively, according to a combined chemotherapy regimen. As an example, the formulations can be for administration in combination with an additional chemotherapeutic agent selected from taxane, taxane derivatives, CPT-11, camptothecin derivatives, anthracycline glycosides, e.g. doxorubicin or epirubicin, etoposide, navelbine, vinblastine, carboplatin, cisplatin and the like, optionally within liposomal formulations thereof In one embodiment, the medicament of the present invention further comprises the said additional chemotherapeutic agent.

In addition to the above, the intravenous estramustine formulations of the invention may also be administered in combination with a bone resorption inhibitor, for instance with the aforementioned bisphosphonates such as clodronate, palmidronate or etridronate.

The invention also provides a product comprising estramustine phosphate and one or more chemotherapeutic agents, optionally within liposomal formulations thereof, and/or a bisphosphonate selected from taxane, taxane derivatives, CPT-11, camptothecin derivatives, anthracycline glycosides, etoposide, navelbine, vinblastine, carboplatin, cisplatin, clodronate, palmidronate and etridronate, as a combined preparation for simultaneous, separate or sequential administration in the inhibition of bone resorption. Such a combined preparation may, for instance, be used for treating, preventing or alleviating the symptoms of bone metastasis.

In accordance with the present invention, the medicament comprising estramustine phosphate may be given once weekly to a maximal dose of 4000 mg or 3000 mg/m$^2$ Another schedule is the administration of a 300–900 mg once a day, for up to 14 days, or twice a week for every two to four weeks.

One schedule may be preferred over another in consideration of schedules with other concomitant therapy.

The present invention will be further illustrated in the following Examples.

EXAMPLE 1

Inhibition of Bone Resorption Using Estramustine Phosphate Sodium.

This example used the organ culture technique with mouse calvaria.
Materials and methods
Test Compound
Estramustine phosphate sodium; estracyt (received from Kabi Pharmacia, Lund, Sweden; Appendix 1).
Reference Compound
Disodium clodronate; Bonefos, Leiras Oy, Turku, Finland.
Bone Resorption Assay
The organ culture technique was used with $^{45}$Ca-prelabeled mouse calvaria. The method has been described by Lerner (1987) and Ljunggren et al. (1991). Newborn mice were injected subcutaneously with $^{45}$CaCl (1.5 μCi/animal). After four days their calvaria were dissected, split into quarters and preincubated in phenol red free CMRL 1066 medium supplemented with 0.1% bovine serum albumin and 50 μg/ml gentamicin for 24 hours at 37° C. in a humidified atmosphere of 5% $CO_2$ in air in the presence of indomethacin (1 μmol/l) and 10 nmol/l bovine parathyroid hormone (PTH). After washing the bone pieces, the medium was changed and cultures incubated for three more days in the same medium but without indomethacin in the presence or absence of estramustine phosphate or clodronate. Resorption was measured by assaying the $^{45}$Ca liberated into the medium using a standard technique for liquid scintillation counting. Total $^{45}$Ca was determined after hydrolysing the calvaria in 6 mol/l HCl overnight. Bone resorption was studied in various concentrations of estramustine phosphate and the effect of estramusine phosphate present only during the preincubation stage was checked in order to study its cytotoxcity.
Results
Estramustine phosphate inhibited bone resorption in this in vitro model concentration-dependently and about as effectively as clodronate. The inhibition percentage was calculated from the parathyroid hormone (PTH)-stimulated $^{45}$Ca release and is shown in Table 1. When estramustine phosphate was present only during preincubation, the inhibition percentages show that at the concentration of 100 μmol/l resorption was strongly inhibited while at the concentration of 10 μmol/l it seemed to be slightly increased (Table 1). In similar experiments clodronate also inhibits resorption.

TABLE 1

Effect of estramustine phosphate on bone resorption in calvaria assay in vitro.

| | Experiment 1 | | Experiment 2 | |
|---|---|---|---|---|
| Concentration, μmol/l | Inhibition % | $^{45}$Ca-release (%) | Inhibition % | $^{45}$Ca-release (%) |
| Estramustine phosphate | | | | |
| 0.01 | 5.5 ± 5.5 | 51.5 ± 3.0 | | |
| 0.1 | 7.2 ± 2.9 | 50.6 ± 1.6 | | |
| 1 | 2.0 ± 5.4 | 55.4 ± 2.9 | | |
| 10 | 34.7 ± 3.1 | 34.7 ± 3.1 | −17.9 ± 8.7 | −47.7 ± 3.5 |
| 100 | 65.3 ± 2.3 | 16.7 ± 0.2 | 70.4 ± 1.4 | 11.9 ± 0.6 |
| 1000 | 55.9 ± 0.6 (precipitate) | 24.0 ± 2.2 | | |
| Clodronate | | | | |
| 0.1 | 0.9 ± 1.2 | | | |
| 1 | 3.5 ± 4.2 | | | |
| 10 | 28.3 ± 3.8 | | | |
| 100 | 51.4 ± 1.9 | | 55.9 ± 0.5 | |
| 1000 | 25.7 ± 6.6 | | | |

Results are expressed as mean±SEM, n=5 or 10. Inhibition percentage was calculated as follows Inhibition %=$^{45}$Ca released control bones (%)–$^{45}$Ca released from sample bones (%) $^{45}$Ca released control bones*100

In calvarial bone resorption assay estramustine phosphate sodium dose-dependently inhibited $^{45}$Ca release, i.e. bone resorption. When the estramustine phosphate was present only during preincubation and after that washed away PTH could not stimulate $^{45}$Ca release from bones. Bisphosphonates which bind to bone and also cytotoxic compounds which do not bind to bone have similar effects in calvarial assay. It can be concluded that estramustine phosphate sodium inhibits bone resorption in vitro in mouse calvaria assay.

EXAMPLE 2

Effect of Estramustine Phosphate and Clodronate on Their Mutual Bioavailability Twelve male patients aged 62–80 were divided into two groups of six patients.
Treatment strategies:
The first group of six patients were given 3200 mg daily of clodronate only for four days. On the fifth day the $AUC_{0-24h}$ for the drug was calculated from serum concentrations of repeated blood samples. On the sixth day, 560 mg estramustine phosphate was add per oral to the clodronate treatment for the following four days. On day ten, the $AUC_{0-24h}$ for both drugs was calculated.

The second group of six patients were give orally 560 mg daily of estramustine phosphate only for four days. On the fifth day the $AUC_{0-24h}$ for the drug was calculated from serum concentrations of repeated blood samples. On the sixth day, 3200 mg clodronate was added to the estramustine phosphate treatment for the following four days. On day ten, the $AUC_{0-24h}$ for both drugs was calculated. The clodronate was provided as 400 mg capsules, and the estramustine phosphate used was estracyt in 140 mg capsules.

The $AUC_{0-24h}$ and $C_{max}$ of clodronate after administration of clodronate alone or clodronate concomitantly with estramustine phosphate (estracyt) did not differ significantly from each other. The $AUC_{0-24h}$ and $C_{max}$ values for estramustine phosphate after administration of estramustine phosphate alone and concomitantly with clodronate, however, differed statistically from each other on the 0.05% level. A summary of $AUC_{0-24h}$ and $C_{max}$ after all treatments is given in the following table:

|  | $AUC_{0-24h}$ | | | | $C_{max}$ | | | |
|  | Clodronate (mg/ml*h) | | Estracyt (μmol/l*h) | | Clodronate (mg/ml) | | Estracyt (Σmol/l) | |
|  | Clodronate only | Clodronate Estracyt | Estracyt only | Estracyt Clodronate | Clodronate only | Clodronate Estracyt | Estracyt only | Estracyt Clodronate |
|---|---|---|---|---|---|---|---|---|
| Mean | 19313.38 | 2.29658e + 11 | 47.38 | 84.74 | 1580.23 | 3376.95 | 3.00 | 5.0 |
| SD | 24510.71 | | 14.63 | 27.68 | 1832.55 | 6506.47 | 0.78 | 1.32 |
| P | | 0.44 | | 0.03 | | 0.46 | | 0.03 |

Estramustine phosphate had no effect on the bioavailability of clodronate whereas the bioavailability of estramustine phosphate was almost doubled when clodronate was added to the therapy.

The method used in the analysis of the serum estramustine phosphate concentrations measures estrone and is insensitive to any metabolites. The estradiol-related metabolites (estramustine and estradiol) were not analyzed in connection with the bioanalysis. However, in Tables 2 and 3, the serum estradiol concentrations of patients 7 to 12 before and after the treatment are given. Unfortunately, estradiol was not measured after administration of estramustine phosphate alone. The results of patients 7, 10 and 12 (560 mg estramustine phosphate during 10 days, 5 last days concomitantly with clodronate) show that the estradiol concentration was increased from a mean of 0.06 mol/l to 27.99 mol/l in patents 8, 9 and 11 (560 mg estramustine phosphate during 5 last days concomitantly with clodronate) from 0.09 mol/l to 5.40 mol/l).

What is claimed is:

1. A method of inhibiting, arresting, or reducing bone resorption, comprising administration of estramustine phosphate to a human being or an animal in which said inhibiting, arresting, or reducing of bone resorption is intended.

2. The method according to claim 1, wherein estramustine phosphate is administered intravenously.

3. The method according to claim 1, wherein estramustine phosphate is administered in combination therapy with an additional chemotherapeutic agent.

4. The method according to claim 1, wherein estramustine phosphate is administered in combination therapy with at least one member selected from the group consisting of taxane, taxane derivatives, CPT-11, camptothecin derivatives, anthracycline glycosides, etoposide, navalbind, vinblastine, carboplatin, and cisplatin.

5. The method according to claim 1, wherein estramustine phosphate is administered in combination therapy with bisphosphonate.

6. The method according to claim 1, wherein estramustine phosphate is administered in combination therapy with at least one member selected from the group consisting of clodronate, palmidronate, and etrigonate.

7. The method according to claim 1, estramustine in the form of an intravenous formulation.

8. The method according to claim 1, wherein estramustine phosphate is administered in combination therapy with a liposomal formulation.

9. The method according to claim 1, wherein the estramustine phosphate is in the form of a freeze-dried formulation.

10. The method according to claim 1, wherein the estramustine phosphate is in the form of a formulation comprising a pharmaceutically acceptable excipient.

11. The method according to claim 10, wherein the pharmaceutically acceptable excipient is at least one member selected from the group consisting of bulking agents, lactose, mannitol, pH buffering agents, antioxidant agents, preservative agents, and tonicity adjusters.

12. A chemotherapeutic regimen, comprising the method according to claim 1.

13. The-method according to claim 1, wherein the patient has at least one cancer selected from the group consisting of prostate cancer, breast cancer, melanoma, lung cancer, pancreatic cancer, colorectal cancer, ovarian cancer, and cancers of the brain.

14. A method of treating, inhibiting, arresting or alleviating the symptoms of a bone resorption disorder comprising the administration of estramustine phosphate to a human being or an animal in which said inhibiting, arresting, reducing, or alleviating the symptoms of a bone resorption disorder is intended.

15. The method according to claim 14, wherein estramustine phosphate is administered intravenously.

16. The method according to claim 14, wherein estramustine phosphate is administered in combination therapy with an additional chemotherapeutic agent.

17. The method according to claim 14, wherein estramustine phosphate is administered in combination therapy with at least one member selected from the group consisting of taxane, taxane derivatives, CPT-11, camptothecin derivatives, anthracycline glycosides, etoposide, navalbind, vinblastine, carboplatin, and cisplatin.

18. The method according to claim 14, wherein estramustine phosphate is administered in combination therapy with bisphosphonate.

19. The method according to claim 14, wherein estramustine phosphate is administered in combination therapy with at least one member selected from the group consisting of clodronate, palmidronate, and etrigonate.

20. The method according to claim 14, wherein the estramustine phosphate is in the form of an intravenous formulation.

21. The method according to claim 14, wherein estramustine phosphate is administered in combination therapy with a liposomal formulation.

22. The method according to claim 14, wherein the estramustine phosphate is in the form of a freeze-dried formulation.

23. The method according to claim 14, wherein the estramustine phosphate is in the form of a formulation comprising a pharmaceutically acceptable excipient.

24. The method according to claim 23, wherein the pharmaceutically acceptable excipient is at least one member selected from the group consisting of bulking agents, lactose, mannitol, pH buffering agents, antioxidant agents, preservative agents, and tonicity adjusters.

25. A chemotherapeutic regimen, comprising the method according to claim 14.

26. The method according to claim 14, wherein the patient has at least one concer selected from the group consisting of prostate cancer, breast cancer, melanoma, lung cancer, pancreatic cancer, colorectal cancer, ovarian cancer, and cancers of the brain.

27. A method of treating, inhibiting, arresting, or reducing bone metastasis, comprising administration of estramustine phosphate to a human being or an animal in which said inhibiting, arresting, or reducing of bone metastasis is intended.

28. The method according to claim 27, wherein estramustine phosphate is administered intravenously.

29. The method according to claim 27, wherein estramustine phosphate is administered in combination therapy with an additional chemotherapeutic agent.

30. The method according to claim 27, wherein estramustine phosphate is administered in combination therapy with at least one member selected from the group consisting of taxane, taxane derivatives, CPT-11, camptothecin derivatives, anthracycline glycosides, etoposide, navalbind, vinblastine, carboplatin, and cisplatin.

31. The method according to claim 27, wherein estramustine phosphate is administered in combination therapy with bisphosphonate.

32. The method according to claim 27, wherein estramustine phosphate is administered in combination therapy with at least one member selected from the group consisting of clodronate, palmidronate, and etrigonate.

33. The method according to claim 27, wherein the estramustine phosphate is in the form of an intravenous formulation.

34. The method according to claim 27, herein estramustine phosphate is administered in combination therapy with a liposomal formulation.

35. The method according to claim 27, wherein the estramustine phosphate is in the form of a freeze-dried formulation.

36. The method according to claim 27, wherein the estramustine phosphate is in the form of a formulation comprising a pharmaceutically acceptable excipient.

37. The method according to claim 36, wherein the pharmaceutically acceptable excipient is at least one member selected from the group consisting of bulking agents, lactose, mannitol, pH buffering agents, antioxidant agents, preservative agents, and tonicity adjusters.

38. A chemotherapeutic regimen, comprising the method according to claim 27.

39. The method according to claim 27, wherein the patient has at least one concer selected from the group consisting of prostate cancer, breast cancer, melanoma, lung cancer, pancreatic cancer, colorectal cancer, ovarian cancer, and cancers of the brain.

* * * * *